United States Patent
Chen et al.

(10) Patent No.: US 9,375,161 B2
(45) Date of Patent: Jun. 28, 2016

(54) SYSTEM AND METHOD FOR DETECTING CARDIAC ARRHYTHMIAS FROM HEART NERVE ACTIVITY

(75) Inventors: Peng-Sheng Chen, Indianapolis, IN (US); Shien-Fong Lin, Indianapolis, IN (US)

(73) Assignee: INDIANA UNIVERSITY RESEARCH & TECHNOLOGY CORPORATION, Indianapolis, IN (US)

( * ) Notice: Subject to any disclaimer, the term of this patent is extended or adjusted under 35 U.S.C. 154(b) by 735 days.

(21) Appl. No.: 13/127,617

(22) PCT Filed: Oct. 28, 2009

(86) PCT No.: PCT/US2009/062300
§ 371 (c)(1),
(2), (4) Date: May 4, 2011

(87) PCT Pub. No.: WO2010/053766
PCT Pub. Date: May 14, 2010

(65) Prior Publication Data
US 2011/0218415 A1 Sep. 8, 2011

Related U.S. Application Data

(60) Provisional application No. 61/112,312, filed on Nov. 7, 2008.

(51) Int. Cl.
*A61M 5/00* (2006.01)
*A61B 5/04* (2006.01)
*A61B 5/00* (2006.01)
(Continued)

(52) U.S. Cl.
CPC ........... *A61B 5/04001* (2013.01); *A61B 5/6846* (2013.01); *A61N 1/3624* (2013.01); *A61N 1/395* (2013.01)

(58) Field of Classification Search
CPC .. A61B 5/04001; A61B 5/6846; A61N 1/395; A61N 1/3624
USPC ...................... 607/3, 6, 9, 14, 62; 604/503, 66
See application file for complete search history.

(56) References Cited

U.S. PATENT DOCUMENTS

| | | |
|---|---|---|
| 5,658,318 A | 8/1997 | Stroetmann et al. |
| 7,266,410 B2 | 9/2007 | Chen |

(Continued)

OTHER PUBLICATIONS

International Searching Authority; International Search Report & Written Opinion for International Application No. PCT/US2009/062300; mailed Dec. 22, 2009 (10 pages).

(Continued)

*Primary Examiner* — Mark W Bockelman
(74) *Attorney, Agent, or Firm* — Quarles & Brady, LLP (57) ABSTRACT

A method has been developed that detects cardiac arrhythmia from intrinsic cardiac nerve signals obtained from a heart in a patient. The method includes sampling intrinsic cardiac nerve activity at a high sample rate, filtering the sampled signal with a high pass filter, comparing the filtered signal to a predetermined threshold, and initiating a therapeutic action in response to the filtered signal exceeding the predetermined threshold. The intrinsic cardiac nerve activity may be received through an electrode implanted on the heart or from an electrode inserted into the venous structure of the heart.

18 Claims, 6 Drawing Sheets

(51) Int. Cl.
*A61N 1/362* (2006.01)
*A61N 1/39* (2006.01)

(56) References Cited

U.S. PATENT DOCUMENTS 7,328,066 B1 2/2008 Levine
2008/0015647 A1 1/2008 Palreddy et al.

OTHER PUBLICATIONS

Chun Hwang et al.; "Vein of Marshall Cannulation for the Analysis of Electrical Activity in Patients With Focal Atrial Fibrillation"; Circulation 101 pp. 1503-1505; 2000 (3 pages).

Simon Dubeau et al.; "Development of a Multi-channel System for Intrinsic Cardiac Neural Recording"; Proceedings of the 28th IEEE EMBS Annual International Conference; Aug. 30, 2006 (4 pages).

SYSTEM AND METHOD FOR DETECTING CARDIAC ARRHYTHMIAS FROM HEART NERVE ACTIVITY

PRIORITY CLAIM

This application claims priority from International Application Number PCT/US09/62300, which is entitled "System And Method For Detecting Cardiac Arrhythmias From Heart Nerve Activity," and which was filed on Oct. 28, 2009. This application claims further priority from U.S. Provisional Application having Ser. No. 61/112,312, which is entitled "System And Method For Detecting Cardiac Arrhythmias From Heart Nerve Activity," and which was filed on Nov. 7, 2008.

GOVERNMENT INTEREST

This invention was made with government support under grants R01 HL71140, R01 HL78932, and P01 HL78931, awarded by the National Institutes of Health. The government has certain rights in the invention.

TECHNICAL FIELD

The invention generally relates to a methods and systems for the prediction of cardiac arrhythmias, and in particular for the prediction of paroxysmal atrial tachycardia and paroxysmal atrial fibrillation.

BACKGROUND

Various cardiac diseases exhibit cardiac arrhythmia. Different treatment options exist for treating the arrhythmia that may arise from these diseases. The most common treatment includes implantable cardiac defibrillators (ICD) and drug therapy. ICDs have been available in the United States since the mid-1980s and have a well-documented success rate in controlling cardiac arrhythmia caused by various heart diseases. An ICD has two basic components: the ICD generator and the lead system for pacing and shock delivery to which it is connected. An ICD generator contains sensing circuits, memory storage, capacitors, voltage enhancers, a telemetry module, and a control microprocessor. Advances in miniaturization and complexity in all of these components have permitted a tremendous reduction in size of the generator itself despite increased functionality, such as added programming options, anti-tachycardia pacing, single- and dual-chamber rate-responsive pacing for bradycardia, biphasic defibrillation waveforms, enhanced arrhythmia detection features, and innovations in lead systems.

Current ICD technology, however, provides for the detection and recognition of an arrhythmia based on the sensed heart rate once it has already started. Although there have been several attempts at developing new technology for predicting the onset of a cardiac arrhythmia, many of these methods and systems appear to rely primarily on events occurring within the heart, such as sensed heart rate and electrocardiography (ECG). For example, one method and device predict cardiac arrhythmias by gathering and processing electrocardiographic data, such as intervals between heart beats (RR-series) or other heart signals, to predict the occurrence of a cardiac arrhythmia. Another method and apparatus forecast arrhythmia based on real-time intact intracardiac electrograms.

In an effort to predict cardiac arrhythmias without reliance on events occurring within a heart, methods and devices have been disclosed that use elevated sympathetic nerve discharges in a patient for cardiac arrhythmia predictions. For example, in U.S. Pat. No. 7,266,410, the disclosed methods and systems generally comprise monitoring the sympathetic neural discharges of a patient from the stellate ganglia, the thoracic ganglia, and/or any other sympathetic nerve identified as having an influence over the heart rate of a patient. Other sympathetic nerves suitable for use in connection with the prediction of cardiac arrhythmias may be generally determined by obtaining simultaneous recordings of neural discharges and heart rate in a test subject and determining whether there exists a correlation between an observed increase in the amplitude and/or frequency of the neural discharges and an increase in heart rate.

Elevated stellate ganglia nerve activity (SGNA) has been demonstrated to precede the onset of cardiac arrhythmias. In one known system, the sympathetic neural discharges may be monitored by a sensor or electrode that is implanted in the stellate ganglia to measure the stellate ganglia nerve activity (SGNA) of the patient from the left stellate ganglion (LSG), the right stellate ganglion (RSG), or both. For example, the electrode may directly sense electrical activity of the stellate ganglia and transmit this data to a processor. The processor may then analyze the data acquired from the electrode and, upon the determination that the SGNA has increased beyond a defined normal value, produce an output signal indicating the likely onset of an arrhythmia, myocardial ischemia, and/or other diseased condition of the heart associated with elevated sympathetic nerve discharges. Another known system compares the parameters for the sensed and normal sympathetic neural discharges in the patient to detect an increase in the sympathetic neural discharge in a patient. An increase in sympathetic neural discharge may also be determined by detecting increases in the amplitude and frequency of the sensed sympathetic neural discharge beyond defined normal values, such as the sensed electrical activity of the stellate ganglia and/or the thoracic ganglia. Predictions of cardiac arrhythmia based on nerve activity from the stellate ganglia are thought to be especially reliable.

While these systems and methods are able to detect an increased likelihood of an occurrence of a cardiac arrhythmia, they do require the implantation of a sensor in the LSG or the RSG, or both. This implantation involves surgery in the vicinity of the spinal column, rather than the heart. Devices that treat cardiac arrhythmia by stimulating myocardial hyperinnervation in the sinus node and right ventricle of the heart of the patient are designed for use with electrodes that have been placed within, but not outside, of the heart. Similarly, devices that apply cardiac pacing, cardioversion, or defibrillation shocks, also use electrodes that are implanted in the heart. Using electrodes coupled to the heart to obtain nerve activity signals, however, is technically difficult because the heart is a strong electrical signal generator. Thus, the detection and monitoring of nerve activity in the noisy environment of the heart is difficult.

SUMMARY

A method has been developed that detects cardiac arrhythmia from intrinsic nerve signals obtained from a heart in a patient. The method includes sampling intrinsic cardiac nerve activity at a high sample rate, filtering the sampled signal with a high pass filter, comparing the filtered signal to a predetermined threshold, and initiating a therapeutic action in response to the filtered signal exceeding the predetermined threshold.

A system that implements this method detects and treats cardiac arrhythmia. The system includes electrodes coupled to intrinsic cardiac nerves, a high frequency signal sampling circuit coupled to the electrodes, the sampling circuit sampling an electrical signal received from the electrodes, a high pass filter coupled to the high frequency signal sampling circuit to filter the sample signal, and a comparator coupled to the high pass filter, the comparator comparing the sampled signal to a predetermined threshold and generating an alarm signal in response to the filtered signal exceeding the predetermined threshold.

In one embodiment, the electrodes are implanted on top of the ligament of Marshall near the pulmonary vein-left atrium junction. The signals obtained by these electrodes are sampled at a high frequency rate, 5,000 times per second, for example, and then high pass filtered to remove the heart electrical activity. The nerve signals to be analyzed are within the frequency range of 0-1000 Hz. The high pass filter, in one embodiment, has a cutoff frequency of 300 Hz. The high pass filtered, digitized signal may then be provided to a processor for analysis and, upon the determination that the nerve signal activity has increased beyond a defined normal value, produce an output signal indicating the likely onset of an arrhythmia, myocardial ischemia, and/or other diseased condition of the heart associated with elevated nerve discharges. The analysis of the nerve signals may be determined by comparing the parameters for the sensed and normal sympathetic neural discharges in the patient. In yet another embodiment, an increase in the neural discharge may be determined by detecting increases in the amplitude and frequency of the sensed neural discharge beyond defined normal values.

A defined normal value represents a value above or beyond which is indicative of an impending arrhythmic, or other diseased condition of the heart previously associated with elevated sympathetic nerve discharges and may be determined with reference to a normal baseline intrinsic cardiac neural discharge. For example, a two-fold or greater increase in the amplitude of the sensed intrinsic cardiac neural discharge from the normal baseline amplitude of the intrinsic cardiac neural discharge may be used as a suitable defined normal value. A second defined normal value may reflect the frequency of intrinsic nerve activity above or beyond which is indicative of an impeding arrhythmic condition of the heart. The defined normal values may be preset or user-defined programmable values.

An output signal may be generated in response to a determined increase in the intrinsic cardiac neural discharge. In one embodiment, the output signal may be an audible sound, a radio-transmitted signal, or any other type of signal that would alert the patient or physician to the possibility of an impending arrhythmia. In another embodiment, the output signal may be an analog or digital command signal directing the delivery of therapy to the patient.

Suitable therapy for use in connection with the methods and systems are known in the art and may include any one or a combination of the following: delivering one or more pharmacological agents, and applying cardiac pacing, cardioversion or defibrillation shocks, to name a few. Any one or more pharmacologic agent(s) may be used in connection with the delivery of therapy. Such pharmacologic agents may include those which are effective in treating cardiac arrhythmias, and any other diseased condition of the heart. Pharmacologic agents which may be used in connection with the delivery of anti-arrhythmic therapy may include, but are not limited to, those which are known to exert anti-arrhythmic effect, such as sodium channel blockers, β-blockers, potassium channel blockers, such as amiodarone and solatol, and calcium channel blockers, such as verapamil and diltiazem. Other suitable pharmacologic agents may include anti-convulsant agents, including but not limited to phenytoin, carbamazepine, valproate, and phenobarbitone, to name a few, which are believed to have anti-arrhythmic effect. One pharmacologic agent that may be used to treat paroxysmal atrial tachycardia (PAT) or paroxysmal atrial fibrillation (PAF) is carvedilol.

The methods and systems described herein may be incorporated into any number of implantable medical devices including, but not limited to, implantable cardiac rhythm management systems such as pacemakers, cardioverters, defibrillators, and the like. The present methods and systems may also be incorporated in external unimplanted devices of the same sort, as well as in external monitors, programmers and recorders. In these cardiac rhythm management devices, the electrodes may be implanted on the heart in an appropriately nerve populated area, such as the Marshall ligament, or inserted via the coronary sinus into the vein of Marshall. The signals may be sampled from the implanted or inserted electrode to detect intrinsic cardiac nerve activities.

The above and other objects, features and advantages will become apparent to those skilled in the art from the following description of the preferred embodiments.

DESCRIPTION OF THE PREFERRED EMBODIMENTS

Methods and systems are disclosed for determining an increased likelihood of the occurrence of a cardiac arrhythmia and other diseased conditions of the heart that are associated with elevated neural discharges in the heart. The methods and systems disclosed herein comprise monitoring neural discharges in a heart, determining an increase in the neural discharges in the heart beyond defined normal values, producing an output signal upon a determined increase in the neural discharges in the heart, and applying therapeutic treatment in response to the output signal. In one embodiment, the output signal may be an audible sound, a radio-transmitted signal, or any other type of signal that would alert the patient or physician to the possibility of an impending arrhythmia or other diseased conditions of the heart. In another embodiment, the output signal may be a command signal directing the delivery of suitable therapy.

Neural discharges in a heart may be monitored by a sensor or electrode that is implanted in the heart near a locus of nerves, such as the vestigial fold of Marshall near the pulmonary vein-left atrium junction, or any other position where the rate of neural discharge influences the heart rate. Alternatively, an electrode may be placed in a patient's heart via a venous structure. For example, the electrode may be placed within the superior or inferior vena cava, the right atrium, the coronary sinus and its branches, including the vein of Marshall using a catheterization process. The sensor or electrode senses the signals corresponding to the neural and heart activity in the area. These signals are sampled at a high frequency rate and high pass filtered to remove signals corresponding to electrical activities of the heart. These filtered data are provided to a processor for immediate processing or to a memory for storage.

Two forms of cardiac nervous activity are Extrinsic Cardiac Nervous Activity (ECNA) and Intrinsic Cardiac Nervous Activity (ICNA). ECNA generally consists of nerve impulses originating in the autonomic nervous system to control the rate at which the heart beats. By contrast, ICNA generally consists of nervous impulses that occur between the various muscles and nerves within the heart itself. The embodiments described herein allow for measuring ICNA activity in vivo.

Figure 1:
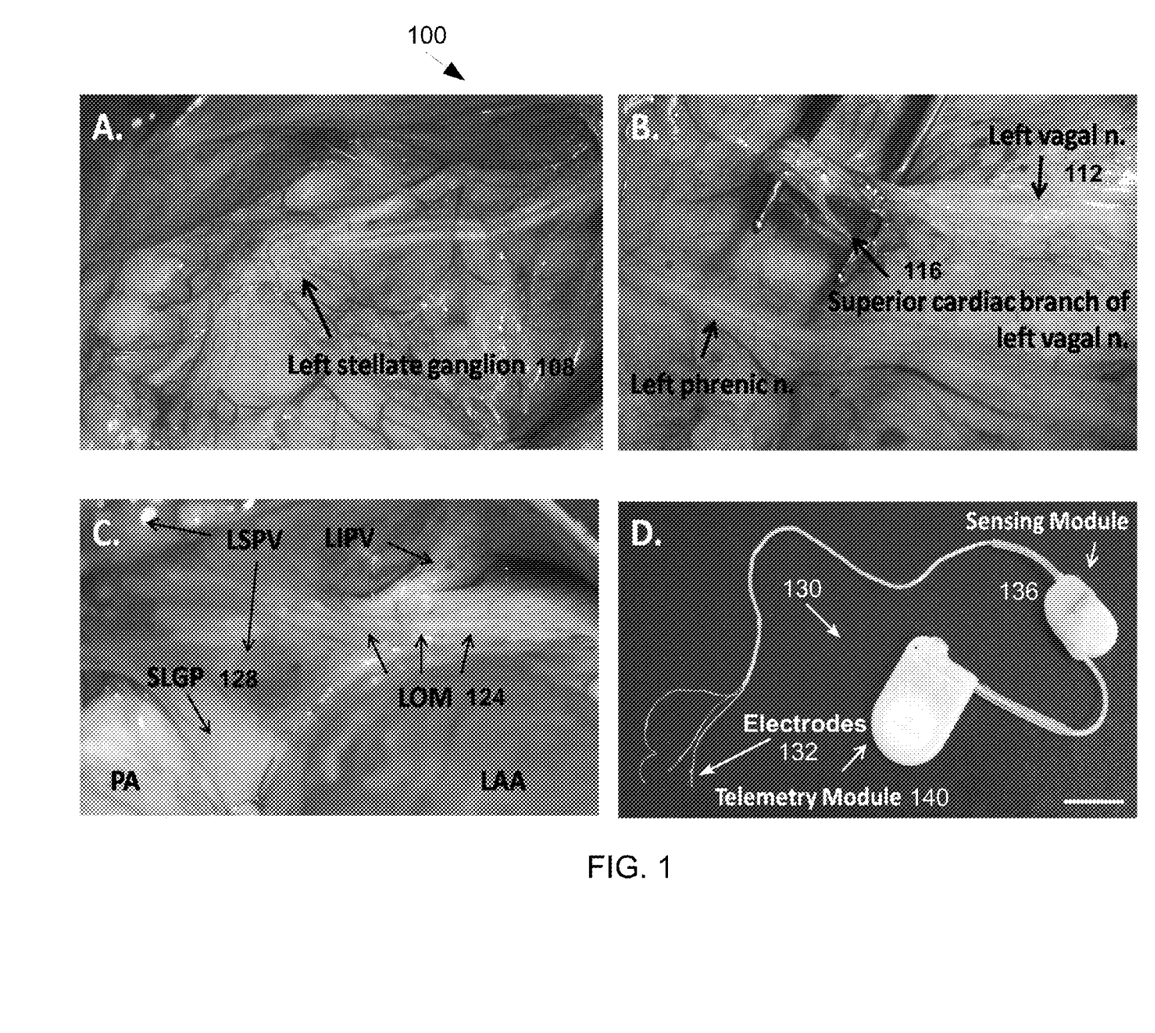
FIG. 1 is a set of photographs showing different nerve locations on a canine heart and an example photograph of a sensor or electrode that measures electrical signals at those locations.

FIG. 1 is a series of photographs 100 including a canine heart depicting the locations of nerves whose activity may be measured for cardia electrical activity. The left stellate ganglion 108 and vagal nerve cavity 112 are both nerves at which extrinsic cardiac nerve activity (ECNA) may be measured by inserting an electrode at these locations. The ligament of Marshall (LOM) nerve 124, and superior left ganglionated plexi nerve (SLGP) 128 are both nerves at which intrinsic cardiac nerve activity (ICNA) may be measured by inserting an electrode at these locations. The final photograph is of an example embodiment of a sensor 130 that may detect electrical signals generated by the cardiac nerves. The sensor has one or more electrodes 132 adapted to being inserted into one or more of the cardiac nerves to record electrical activity. The sensing module 136 detects and records this activity. In the present embodiments, after data are recorded from the sensing unit and relayed via the telemetry unit 140 to an external signal processor, further signal processing, such as digitizing, filtering, or amplifying the data, may be used to display desired portions of cardiac nervous activity. This signal processing is carried out externally from the sensor, and, in one example, an embodiment may include a signal processor that executes software programs stored in the memory of the processor or loaded from physical recorded media to process the signals received from the telemetry unit. In other embodiments, the sensor module may amplify or filter the electrical signal before it is transmitted from the sensor device to an external device. In still other embodiments, both the sensing module and external signal processing systems may process the electrical signal. The telemetry module relays the information detected by the sensor to external recording equipment. In the example embodiment, this telemetry module may transmit data as a radio signal, with one particular advantage being that the entire measuring device may be placed entirely within the test subject's thoracic cavity.

Figure 2:
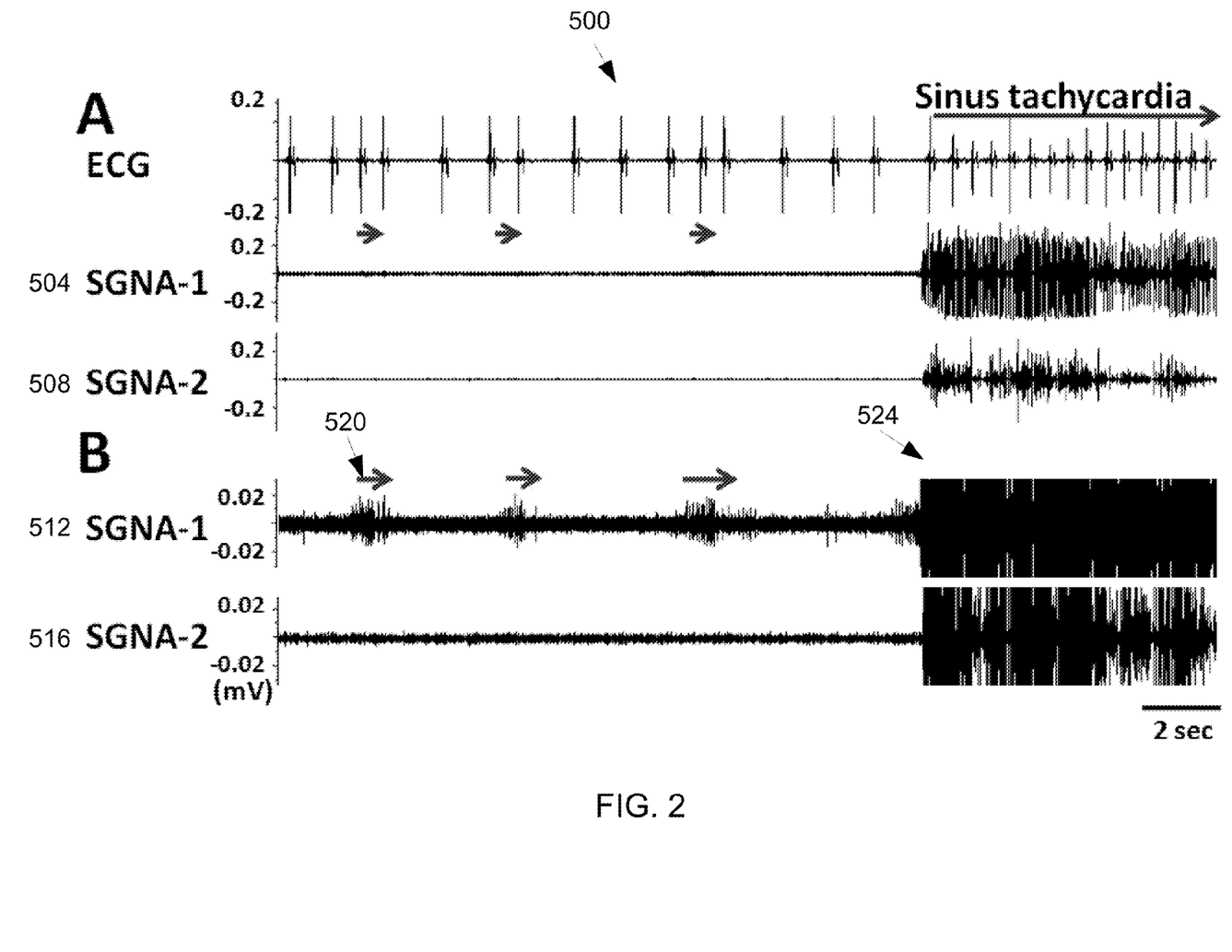
FIG. 2 is a diagram showing the outputs of an existing radiotransmitter and an improved radiotransmitter in detecting electrical signals generated by stellate ganglion nerve activity (SGNA).
Figure 3:
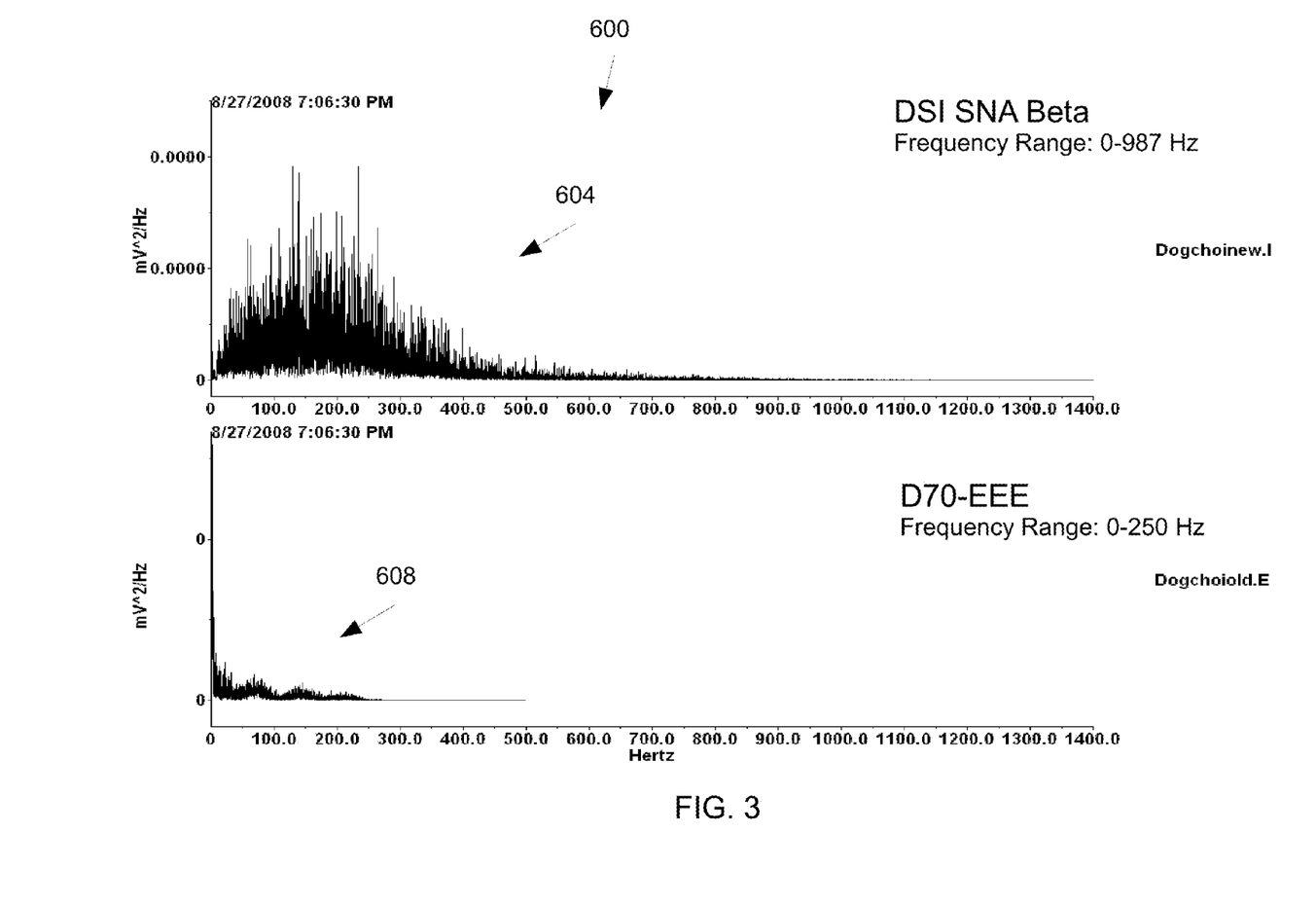
FIG. 3 is a diagram showing the frequency responses of an existing radiotransmitter and an improved radiotransmitter while recording electrical signals generated by stellate ganglion nerve activity during a period of tachycardia.

Two possible embodiments of sensors capable of recording electrical signals from cardiac activity are the Data Sciences Inc. (DSI) D70-EEE, and a prototype model DSI SNA beta sensor. The D70-EEE is a commercially available radiotransmitter that is designed to receive signals with frequencies between 0 and 250 Hz, with a sampling rate of 1 KHz. The DSI SNA model represents an improvement designed to receive signals with frequencies between 0 and 1000 Hz, with a sampling rate of 5 KHz. FIG. 2 is a graph of signal outputs 500 of each sensor when measuring electrical signals generated by stellated ganglion nervous activity (SGNA) immediately prior to an episode of tachycardia. SGNA-1 represents the signal from the improved DSI SNA radiotransmitter, while SGNA-2 represents the signal from the older D70-EEE model. The signals in section A appear similar, but section B depicts amplification of both signals that shows the DSI SNA sensor detects SGNA nerve activity 520 prior to the onset of the tachycardia event 524. The older D70-EEE radiotransmitter fails to detect the pre-tachycardia SGNA events. FIG. 3 shows operational frequency responses 600 from each radiotransmitter, with the DSI SNA response 604 covering a range of 0-987 Hz and the D70-EEE response 608 only covering 0-250 Hz. While the DSI SNA radiotransmitter has desirable characteristics, its description is not intended to exclude other devices, and is merely illustrative of an improved radiotransmitter device. Any sensor and transmitter with similar or superior frequency response and sampling rate characteristics that are adapted for in vivo monitoring could be substituted for the DSI SNA radiotransmitter discussed herein.

Canine test subjects were fitted with both the D70-EEE and DSI SNA radiotransmitters attached to electrodes that were placed around the test subject's heart. As a baseline, the D70-EEE was attached to the stellate ganglia, vagal, ligament of Marshall, and superior left ganglionated plexi nerves. The DSI SNA radiotransmitter was attached to the stellate ganglia, vagal, and ligament of Marshall nerves. Canines were chosen because the extrinsic and intrinsic cardiac nerve activity of canines is similar to that of humans. The stellate ganglia and vagal probes measure extrinsic activity to form a baseline, and the ligament of Marshall and superior left ganglionated plexi probes enabled the capabilities of existing radiotransmitters, such as the the D70-EEE radiotransmitter, to be compared with improved radiotransmitters, such as the DSI SNA radiotransmitter. The measurement procedure begins with collection of signals from each nerve to establish a baseline. Then, using known techniques to stimulate the monitored heart, the test subject's heart undergoes atrial tachycardia followed by an atrial fibrillation event. The process of inducing tachycardia, atrial fibrillation, and then allowing the cardiac rhythm to return to normal was repeated over the course of several weeks.

While the D70-EEE can detect abnormal electrical signals generated by ECNA prior to some arrhythmia events in an ambulatory test subject, this sensor cannot detect ICNA signals from the ligament of Marshall. Using the techniques described herein, the DSI SNA radiotransmitter detected ICNA signals in an ambulatory canine that were not previously detectable. The comparison tests showed that while the D70-EEE could detect ECNA signals and some ICNA signals from the superior left ganglionated plexi, it failed to detect the full frequency range of ICNA signals that the DSI SNA sensor was able to detect. In particular, the frequency response and the high band pass filtering capabilities enabled the DSI SNA radiotransmitter to detect electrical signals generated in the ligament of Marshall that were not detectable in vivo with the D70-EEE.

Figure 4:
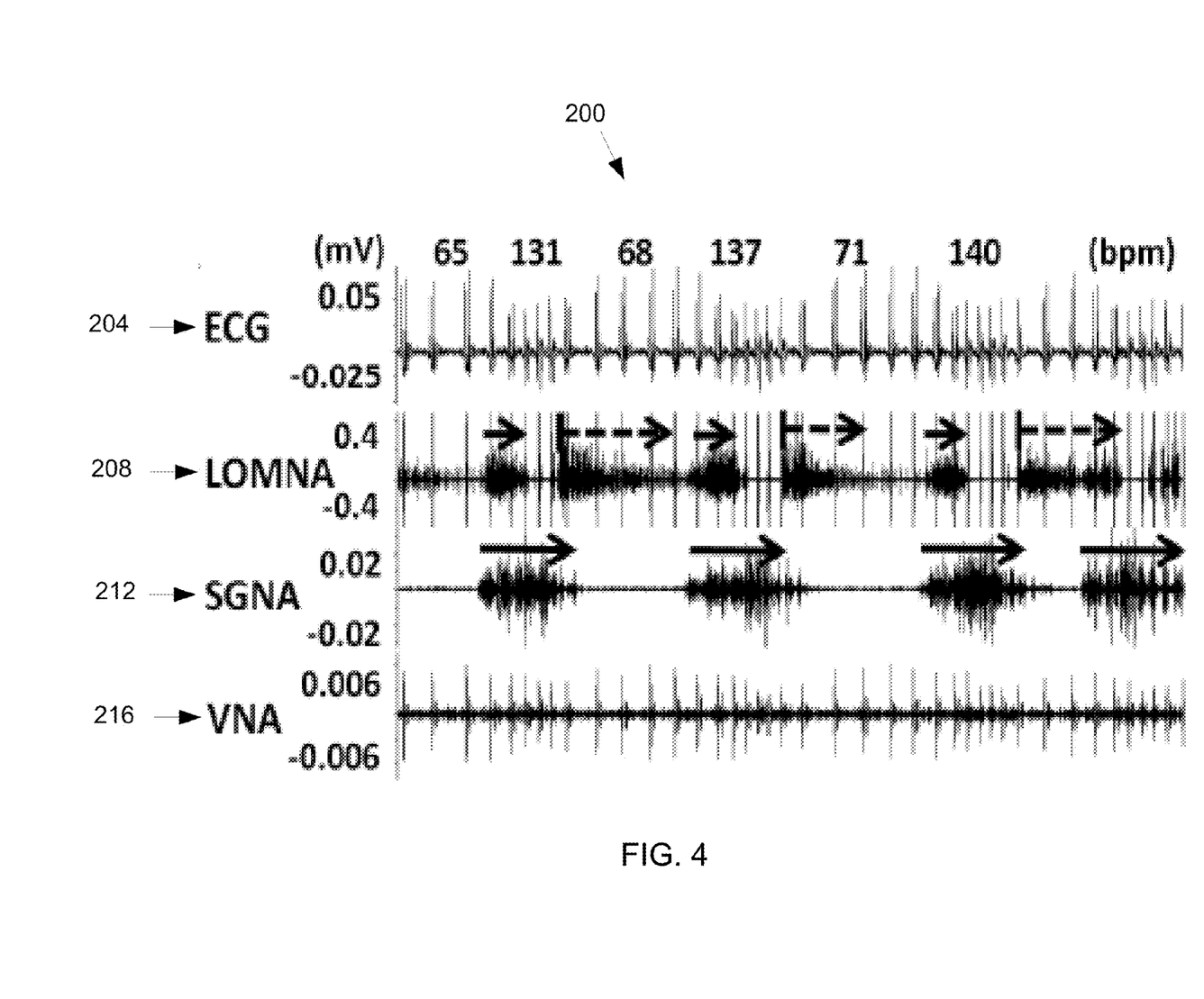
FIG. 4 is a graph of detected electrical signals generated by intrinsic and extrinsic nervous activity.

FIG. 4 is a graph 200 showing both ICNA and ECNA signals that the DSI SNA sensor detected while measuring the test subject's cardiac nervous activity. The ECG 204 is measured externally by known means and is provided in the figure for reference to indicate the pacing of the test subject's heartbeat. The LOMNA graph 208 indicates electrical signals generated by intrinsic nerves that were detected from the ligament of Marshall. Thus, these signals are examples of ICNA. The SGNA graph 212 and VNA graph 216 reveal that the DSI SNA radiotransmitter was also able to detect the electric signals occurring in stellate ganglia and vagal nerves caused by ECNA.

Data acquired from the sensor or electrode is filtered to remove signals associated with the electrical activity of the heart. The amplitude of a signal from a sympathetic nerve is typically −2 to +2 mV and the electrode noise is on average 10 μV for an ideal electrode resistance between 100 kΩ and 10 MΩ at 37° C. for a bandwidth of 1 kHz. Much of the noise during in vivo recording results from electrical activity of the heart. Cross-talk from parasitic capacitances may also result in the generation of unwanted signals when using conventional electrodes to record neural discharges. A wide band pass filter (1 to 3000 Hz) allows recording of neural discharges, but also enables a significant amount of noise generated by cardiac and respiratory related movement artifacts to be detected as well. A high pass filter with a cutoff frequency of approximately 300 Hz removes most of the noise and achieves a more stable baseline of the recorded neural discharge signals.

The data acquired from the sensor may be continuously monitored to detect increases in the neural discharges. In one embodiment, an increase in the neural discharges in the patient may be determined by detecting an increase in the amplitude and frequency of the sensed neural discharges beyond defined normal values. Since a normally functioning heart generates a baseline electrical noise level, nerve activity indicative of atrial tachycardia or atrial fibrillation in one embodiment is defined as a 3-fold increase in the amplitude of electrical signals over the baseline electrical noise level. In another embodiment, an increase in the neural discharges in the patient may be determined by comparing the parameters for the sensed neural discharges in the patient with the parameters defined for normal neural discharges. In an alternative embodiment, a wire electrode may be used to obtain cardiac nerve activity recordings. Such recordings may be obtained from stainless steel wires terminating in a locus of nerves in the heart and connected to the transmitter at its other end.

Figure 5:
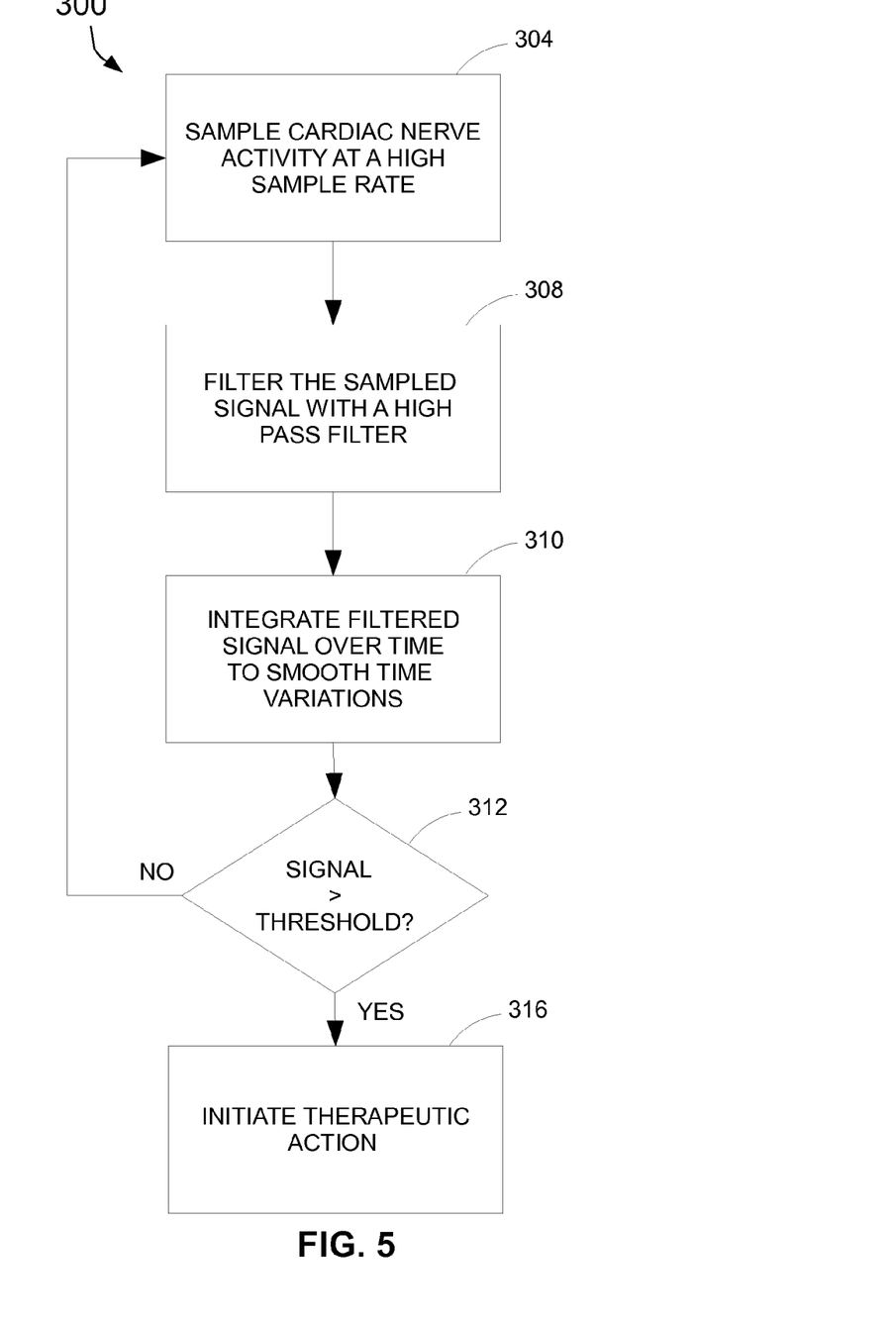
FIG. 5 is a block diagram of a method for detecting cardiac arrhythmia from cardiac nerve activity.

A method for detecting cardiac arrhythmia is shown in FIG. 5. The process 300 obtains samples of cardiac nerve activity at a high sample rate from electrodes implanted in the monitored heart (block 304). A sample rate of at least 5000 samples per second has been used in one embodiment. The sampled signal is then filtered with a high pass filter (block 308) to remove the signals associated with heart and respiratory movement. A high pass filter having a cutoff frequency of 300 Hz has proven effective in canine studies. The filtered signal is integrated to smooth the signal over time and reduce the likelihood of a false alarm signal (block 310). The integrated signal is compared to a predetermined threshold (block 312) to determine whether a cardiac arrhythmia appears imminent. The predetermined threshold may be a signal amplitude or frequency that has been empirically established. Therapeutic action is initiated in response to the filtered signal exceeding the predetermined threshold (block 316). Otherwise, the process continues to monitor the cardiac nerve activity. While the threshold and therapeutic action may be directed to cardiac arrhythmia, other abnormalities may be detected with attendant actions taken as well.

The defined normal value or threshold represents a value above and beyond which is indicative of an impending arrhythmic condition of the heart and may be determined with reference to the normal baseline neural discharges. For example, a two-fold or greater increase in the amplitude of the sensed neural discharge from the normal baseline amplitude of a neural discharge may be used as a suitable defined normal value. A second defined normal value with respect to the frequency of the neural discharge may be similarly provided. The defined normal values may be a preset or user-defined programmable value.

Once an increase in the neural discharges has been determined, the therapeutic action may include the generation of an output signal. In one embodiment, the output signal may be an audible sound, a radio-transmitted signal, or any other type of signal that would alert the patient or physician to the possibility of an impending arrhythmia or other diseased condition of the heart associated with elevated neural discharge. Upon the generation of the output signal, the patient or physician may then take precautionary or therapeutic measures to avoid or reduce the likelihood of an impending cardiac arrhythmia or other diseased condition of the heart.

In another embodiment, the output signal may be a command signal directing the delivery of suitable therapy. Suitable therapy for use in connection with the methods and systems are known in the art and may include any one or a combination of the following: delivering one or more pharmacological agents, and other actions such as cardiac pacing, cardioversion, or defibrillation shocks. A suitable drug delivery system for an implantable cardiac device is disclosed in U.S. Pat. No. 6,361,522, which is incorporated herein in its entirety.

Pharmacologic agents may include those which are known to exert an anti-arrhythmic effect, such as sodium channel blockers, β-blockers, potassium channel blockers, such as amiodarone and solatol, and calcium channel blockers, such as verapamil and diltiazem. Other suitable anti-arrhythmic pharmacologic agents include anti-convulsant agents, such as phenytoin, carbamazepine, valproate, and phenobarbitone. The nerves near the vestigial fold of Marshall, for example, are capable of high frequency neuronal discharges and these discharges directly increase heart rate. Anti-convulsants work by selectively suppressing high frequency neuronal discharges in the central and peripheral nervous system. Anti-convulsants are also known to suppress cardiac sympathetic nerve discharges. Because of the importance of the autonomic nervous system in arrhythmogenesis, drugs that prevent the release of adrenergic neurotransmitters may thereby decrease the sympathetic outflow are useful for controlling cardiac arrhythmia. For example, phenytoin has been shown to suppress cardiac arrhythmia induced by digitalis toxicity. The action of phenytoin is related to use- and frequency-dependent selective suppression of high-frequency neuronal activity. The molecular mechanism for this is a voltage-dependent blockade of membrane sodium channels responsible for the action potential. Through this action, phenytoin obstructs the positive feedback that underlies the development of maximal seizure activity.

Another class of pharmacologic agents that may be used are neurohormonal antagonists that combine β-blocker and α-blocker properties. One such agent is carvedilol, which is known to block the $\beta_1$-, $\beta_2$-, and α-adrenoreceptor, and to possess anti-oxidant and calcium antagonist properties. An example treatment program administered 12.5 mg doses of carvedilol twice daily for seven days to canine test subjects, but the dosages and lengths of time may vary for different subjects. Short-term use of carvedilol was found to suppress increases the integrated ECNA and ICNA that lead to atrial fibrillation. The carvedilol's effects ceased shortly after treatments stopped, and the integrated nervous activity subsequently increased to levels higher than before the carvedilol treatment began.

Anti-convulsants may block the cardiac nerve discharges through two actions. One is frequency-dependent block of sodium currents and the second is a block of calcium currents.

A combined channel blockade may account for the effects of anticonvulsant drugs. In addition to epilepsy, anti-convulsants, such as phenytoin and carbamazepine, are also useful in treating neuropathic pain, which is characterized by abnormal spontaneous and increased evoked activity from damaged areas of the peripheral nervous system. Other suitable pharmacologic agents may also be used for the treatment of myocardial ischemia and may include, but are not limited to, statins, angiotensin-converting enzyme (ACE) inhibitors, aspirin, beta blockers, calcium channel blockers, and nitrates. Any other suitable pharmacologic agent, that is known to treat a diseased condition of the heart associated with elevated cardiac neural discharges, may be used in combination with any other pharmacologic agent and/or therapy.

Figure 6:
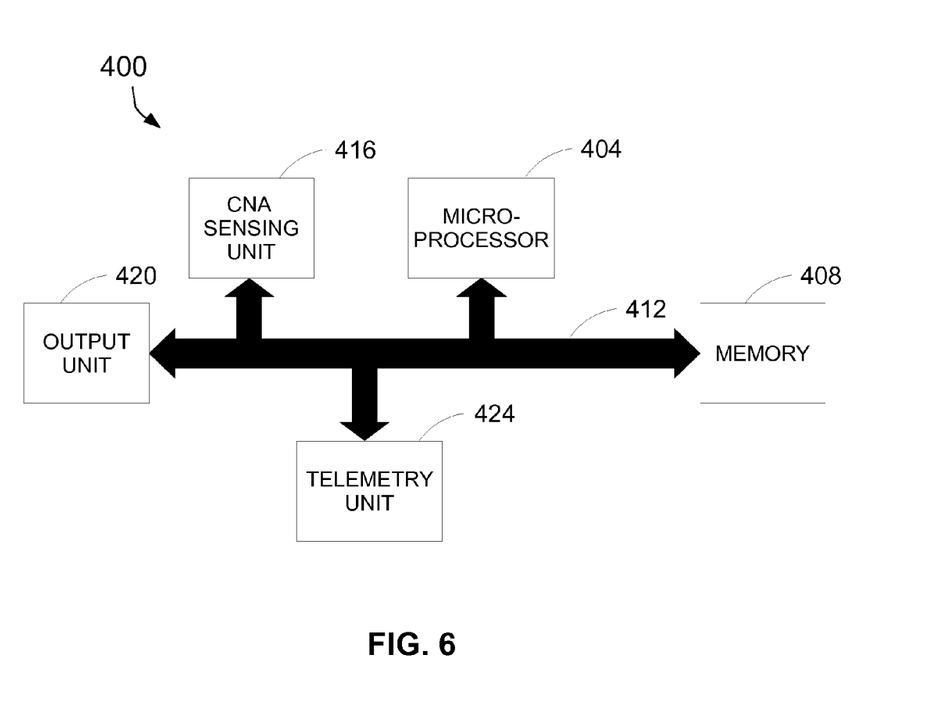
FIG. 6 is a block diagram of system that detects cardiac arrhythmia from cardiac nerve activity.

The methods disclosed herein may be carried out by a programmable implantable or external device, including, but not limited to, implantable cardiac rhythm management systems such as pacemakers, cardioverters, ICDs, and the like. A block diagram for an example of such a device is shown in FIG. 6. As shown there, the device 400 may comprise a microprocessor 404, a memory 408, a bi-directional data bus 412, a cardiac nerve activity (CNA) sensing unit 416, an output unit 420, and a telemetry interface 424.

The microprocessor 404 may communicate with the memory 408 through the data bus 412 and execute a program stored in the memory. The microprocessor may internally include an analog-to-digital converter (ADC) having a high sampling rate or the CNA sensing unit 416 may include the high frequency signal sampling circuit that collects data from the nerves in the heart of a patient. The sensing unit 416 includes electrodes that are implanted in the heart to obtain electrical signals from the heart. After the sampled signal is high pass filtered, these data may then be transmitted over the bus 412 to the microprocessor 404 for immediate processing or to the memory 408 for storage and subsequent processing as appropriate. In one embodiment, the ADC has a sampling rate of 5,000 times per second. Furthermore, the processor includes instructions for digitally processing the sampled signal to filter the sampled signal with a high pass filter. In one embodiment, the cutoff frequency for the high pass filter is 300 Hz. The microprocessor 404 may also execute programming instructions resident in memory to identify increases in the neural discharges in the heart of the patient and command the output unit to produce an output signal in response to those identified increases that meet or exceed a predetermined threshold.

The memory 408 may comprise any suitable combination of read-only memory (ROM) containing the device operating software, random access memory (RAM) for data storage, and on-board or off-board cache memory associated with the microprocessor. The data bus 412 permits communication between the microprocessor 404, memory 408, CNA sensing unit 416, output unit 420, and the telemetry interface 424. The telemetry interface 424 may be used for downloading stored data to an external programmer and for receiving telemetry data from the programmer to modify programmable parameters and/or change the device operating software.

The CNA sensing unit 416 may comprise one or more electrodes or sensors coupled to nerves in the heart of the patient, such as those at the vestigial fold of Marshall, and interface circuits that receive and process the sensed signals from the electrodes. Accordingly, the CNA sensing unit may receive electrical signals from the nerves in the heart of the patient, filter those signals, and convert them into digital data or otherwise make the data available to the microprocessor. The output unit 420 includes a therapeutic signal generator coupled to the processor 404. As noted above, the processor 404 includes processing that implements a comparator to detect the filtered nerve signal exceeding a predetermined threshold. In response to the predetermined threshold being exceeded, the therapeutic signal generator generates a signal that initiates therapeutic activity for the impending cardiac arrhythmia. These activities include, for example, generation of a signal that stimulates nerves of the monitored heart, such as a signal that applies one of cardiac pacing, cardioversion, or defibrillation shocks to a heart, or a signal that causes another device to deliver at least one pharmacological agent to a heart.

Those skilled in the art will recognize that numerous modifications can be made to the specific implementations of the ink umbilical described above. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

What is claimed:

1. A method for detecting and treating cardiac events comprising:
   sampling, using an electrode positioned within a heart to receive cardiac nerve activity, intrinsic cardiac nerve activity at a high sample rate;
   filtering the sampled signal with a high pass filter;
   comparing the filtered signal to a predetermined threshold; and
   initiating a therapeutic action in response to the filtered signal exceeding the predetermined threshold.

2. The method of claim 1, wherein the cardiac nerve activity being sampled has a bandwidth of 1000 Hz.

3. The method of claim 1, the sampling of the cardiac nerve activity further comprising:
   sampling the cardiac nerve activity at a rate of at least 5000 samples per second.

4. The method of claim 1, the high pass filtering of the sampled signal further comprising:
   filtering the sampled signal with a high pass filter having a cutoff frequency of 300 Hz.

5. The method of claim 1, wherein the predetermined threshold is a predetermined signal amplitude.

6. The method of claim 1, wherein the predetermined threshold is a predetermined frequency.

7. The method of claim 1, the therapeutic action comprising:
   delivering at least one pharmacological agent to a heart.

8. The method of claim 1, the therapeutic action comprising:
   applying one of cardiac pacing, cardioversion, or defibrillation shocks to a heart.

9. The method of claim 1, the therapeutic action comprising:
   delivering carvedilol in an effective amount to a heart.

10. A system for detecting and treating cardiac events comprising:
    electrodes configured to be positioned within a heart and adapted to be coupled to intrinsic cardiac nerves in the heart;
    a high frequency signal sampling circuit coupled to the electrodes, the sampling circuit configured to sample intrinsic nerve signals received from the electrodes;
    a high pass filter, coupled to the high frequency signal sampling circuit, having a cutoff frequency of approximately 300 Hz configured to at least filter artifacts associated with cardiac activity from the sampled intrinsic nerve signals; and a comparator coupled to the high pass filter, the comparator comparing the filtered signals to a predetermined threshold and generating an alarm signal in response to the filtered signals exceeding the predetermined threshold.

11. The system of claim 10, wherein the electrodes are stainless steel wires.

12. The system of claim 10, the high frequency sampling circuit sampling the signal received from the electrodes at a rate of at least 5000 samples per second.

13. The system of claim 10, the predetermined threshold corresponding to a predetermined amplitude.

14. The system of claim 10, the predetermined threshold corresponding to a predetermined frequency.

15. The system of claim 10 further comprising:

a therapeutic signal generator coupled to the comparator, the therapeutic signal generator generating a therapeutic signal in response to the alarm signal.

16. The system of claim 15, the therapeutic signal delivering at least one pharmacological agent to the heart.

17. The system of claim 16, the therapeutic signal applying one of cardiac pacing, cardioversion, or defibrillation shocks to the heart.

18. The system of claim 16 wherein the at least one pharmacological agent includes carvedilol.

* * * * *